(12) United States Patent
Cho et al.

(10) Patent No.: US 10,512,776 B2
(45) Date of Patent: Dec. 24, 2019

(54) BODY STIMULATING STRUCTURE COMPRISING COIL EMBEDDED THEREIN

(71) Applicant: KOREA INSTITUTE OF SCIENCE AND TECHNOLOGY, Seoul (KR)

(72) Inventors: Jeiwon Cho, Seoul (KR); Jinseok Kim, Seoul (KR); Hyungdal Park, Seoul (KR); Yeowool Huh, Seoul (KR)

(73) Assignee: KOREA INSTITUTE OF SCIENCE AND TECHNOLOGY, Seoul (KR)

(\*) Notice: Subject to any disclaimer, the term of this patent is extended or adjusted under 35 U.S.C. 154(b) by 0 days.

(21) Appl. No.: 15/672,297

(22) Filed: Aug. 9, 2017

(65) Prior Publication Data
US 2018/0043156 A1   Feb. 15, 2018

(30) Foreign Application Priority Data
Aug. 11, 2016  (KR) .................. 10-2016-0102491

(51) Int. Cl.
*A61N 1/36*    (2006.01)
*A61H 23/02*   (2006.01)
*A61N 2/00*    (2006.01)
*A61N 1/05*    (2006.01)
*A61N 1/372*   (2006.01)

(52) U.S. Cl.
CPC ....... *A61N 1/3606* (2013.01); *A61H 23/0218* (2013.01); *A61N 2/002* (2013.01); *A61N 2/006* (2013.01); *A61N 1/0529* (2013.01); *A61N 1/36082* (2013.01); *A61N 1/372* (2013.01)

(58) Field of Classification Search
CPC ........ A61N 2/02; A61N 2/002; A61N 1/0529; A61N 1/0531; A61N 1/3606
See application file for complete search history.

(56) References Cited

U.S. PATENT DOCUMENTS 5,010,897 A \* 4/1991 Leveen .................. A61N 1/403
                                              600/13
7,010,351 B2   3/2006 Firlik et al.
8,277,371 B2   10/2012 Zangen et al.

FOREIGN PATENT DOCUMENTS

JP    2009202020 A    9/2009
KR    1020080100573 A  11/2008

\* cited by examiner

*Primary Examiner* — Joseph M Dietrich
(74) *Attorney, Agent, or Firm* — Cantor Colburn LLP

(57) ABSTRACT

A body stimulating structure includes a body which is attached to an internal organ of a living body, and a magnetic field inductor formed in the body, wherein when power is supplied, the magnetic field inductor produces a magnetic field and applies magnetic stimulation to a target site of the internal organ of the living body to which the body is attached. A method for manufacturing the body stimulating structure includes: forming a first pattern on a first substrate and filling the first pattern with a conductor; stacking a second substrate on the first substrate; and forming a second pattern connected to the first pattern on the second substrate and filling the second pattern with a conductor.

13 Claims, 6 Drawing Sheets

BODY STIMULATING STRUCTURE COMPRISING COIL EMBEDDED THEREIN

CROSS-REFERENCE TO RELATED APPLICATION

This application claims priority to Korean Patent Application No. 10-2016-0102491, filed on Aug. 11, 2016, and all the benefits accruing therefrom under 35 U.S.C. § 119, the contents of which in its entirety are herein incorporated by reference.

BACKGROUND

1. Field

The present disclosure relates to a body stimulating structure, and more particularly, to a body stimulating structure that is attached to an internal organ of a living body to apply stimulation such as magnetic stimulation and electrical stimulation to an attachment site and obtain signals generated from the stimulated organ.

DESCRIPTION ABOUT NATIONAL RESEARCH AND DEVELOPMENT SUPPORT

This study was supported by the Individual Research Support of Ministry of Science, ICT and Future Planning, Republic of Korea (Project No. 1711037459) under the superintendence of National Research Foundation of Korea.

2. Description of the Related Art

Recently, to treat various brain diseases and understand the working mechanism of the brain, studies on technology to stimulate the cranial nerves with various stimulation means, and sense and analyze neural signals emitted from the cranial nerves due to the stimulation are being actively made.

Methods for stimulating the cranial nerves include electrical stimulation to stimulate the cranial nerves by applying an electric current, drug stimulation to stimulate the cranial nerves by injecting a fluid, optical stimulation to stimulate the cranial nerves with optical radiation, and magnetic stimulation to stimulate the cranial nerves by changing the strength of a magnetic field. The cranial nerves in a target site are artificially stimulated using the stimulation means, and neural signals emitted from the cranial nerves in response to the stimulation are collected.

Among the cranial nerve stimulation means, electrical stimulation, drug stimulation, and optical stimulation stimulates the cranial nerves by directly inserting a neural probe manufactured to a small scale via micromachining technique into the brain, to transmit each stimulation medium without causing great damage when inserted into the brain.

The electrical stimulation stimulates the cranial nerves by emitting electrical signals from electrodes connected up to the distal end of the neural probe. The drug stimulation stimulates the cranial nerves by injecting drugs into the brain through microfluidic channels formed in the neural probe. The optical stimulation stimulates the cranial nerves with light irradiation into the brain through an optical waveguide provided in the neural probe. As described above, it is possible to directly stimulate a target site through the neural probe inserted into the brain.

However, in the case of electrical stimulation, because the material itself consisting of the brain is conductive, focal stimulation of the cranial nerves is difficult and there is a risk of damage to the cranial nerves. Furthermore, in the case of optical stimulation, stimulation of the cranial nerves with light irradiation requires transfection of specific genes that are activated and deactivated by a specific wavelength of light, leaving problems to be solved for future clinical applications.

On the other hand, an advantage of magnetic stimulation is that it is possible to stimulate the cranial nerves from the outside of the skull through a device for magnetic stimulation formed of a metal coil without any surgery, but on the contrary, a disadvantage is that it is difficult to localize stimulation of cranial nerves in a target site, and in the case of deep brain regions, it is very difficult to increase the focality of magnetic stimulation. To overcome the disadvantage of magnetic stimulation, metal coil models having various shapes and designs have been proposed, but focal stimulation of deep brain regions is still difficult.

Accordingly, there is a growing need for magnetic stimulation means for localizing stimulation of the cranial nerves to increase focality while minimizing cranial nerve damage caused by stimulation, and collecting signals in response to the stimulation.

SUMMARY

The present disclosure is directed to providing a body stimulating structure in which a body comprising a conducting coil embedded therein is attached to an internal organ of a living body, an electric current is applied to the coil to produce a magnetic field, magnetic stimulation is delivered locally to an attachment site, and response signals are collected.

To achieve the object, a body stimulating structure according to an embodiment of the present disclosure includes: a body which is attached to an internal organ of a living body; and a magnetic field inductor formed in the body, wherein when power is supplied, the magnetic field inductor produces a magnetic field and applies magnetic stimulation to a target site of the internal organ of the living body to which the body is attached.

According to an embodiment of the present disclosure, the magnetic field inductor may be a coil.

According to an embodiment of the present disclosure, the body stimulating structure may include a plurality of coils arranged in parallel, spaced apart from each other.

According to an embodiment of the present disclosure, the plurality of coils may be arranged such that axial directions of the coils are perpendicular to a surface of the internal organ of the living body to which the body is attached.

According to an embodiment of the present disclosure, an electric current may flow individually in the plurality of coils, and all or some of the plurality of coils may be selected to apply magnetic stimulation to the internal organ of the living body.

According to an embodiment of the present disclosure, each of the plurality of coils may be placed close to each other as a pair at each location on the body to form pairs.

According to an embodiment of the present disclosure, the body may be made of a flexible material.

According to an embodiment of the present disclosure, the body may be attached to the internal organ of the living body such that axial directions of the coils are perpendicular to a surface of the internal organ of the living body.

According to an embodiment of the present disclosure, the body stimulating structure may further include an electrode provided in the body to obtain a bio-signal generated in response to the magnetic stimulation.

According to an embodiment of the present disclosure, electrical stimulation may be applied to the internal organ of the living body through the electrode.

According to an embodiment of the present disclosure, the body stimulating structure may further include a temperature sensor provided in the body to measure an internal temperature of the living body.

To achieve the object, a method for manufacturing the body stimulating structure according to another embodiment of the present disclosure includes: forming a first pattern on a first substrate and filling the first pattern with a conductor; stacking a second substrate on the first substrate; and forming a second pattern connected to the first pattern on the second substrate and filling the second pattern with a conductor, wherein the first substrate and the second substrate form the body, and the conductor of the first pattern and the conductor of the second pattern form the parts of the magnetic field inductor.

According to an embodiment of the present disclosure, the magnetic field inductor may be formed in a shape of a coil.

According to an embodiment of the present disclosure, the conductor of the first pattern may be a first coil turn of the coil of an open loop type, the conductor of the second pattern may be a first coil pillar extending upwards from one end of the first coil turn, and the method may further include stacking one or more substrates including one of remaining coil turns of the coil of an open loop type and coil pillars electrically connecting each coil turn in an alternating manner on the second substrate in a sequential order.

DETAILED DESCRIPTION

Figure 1:
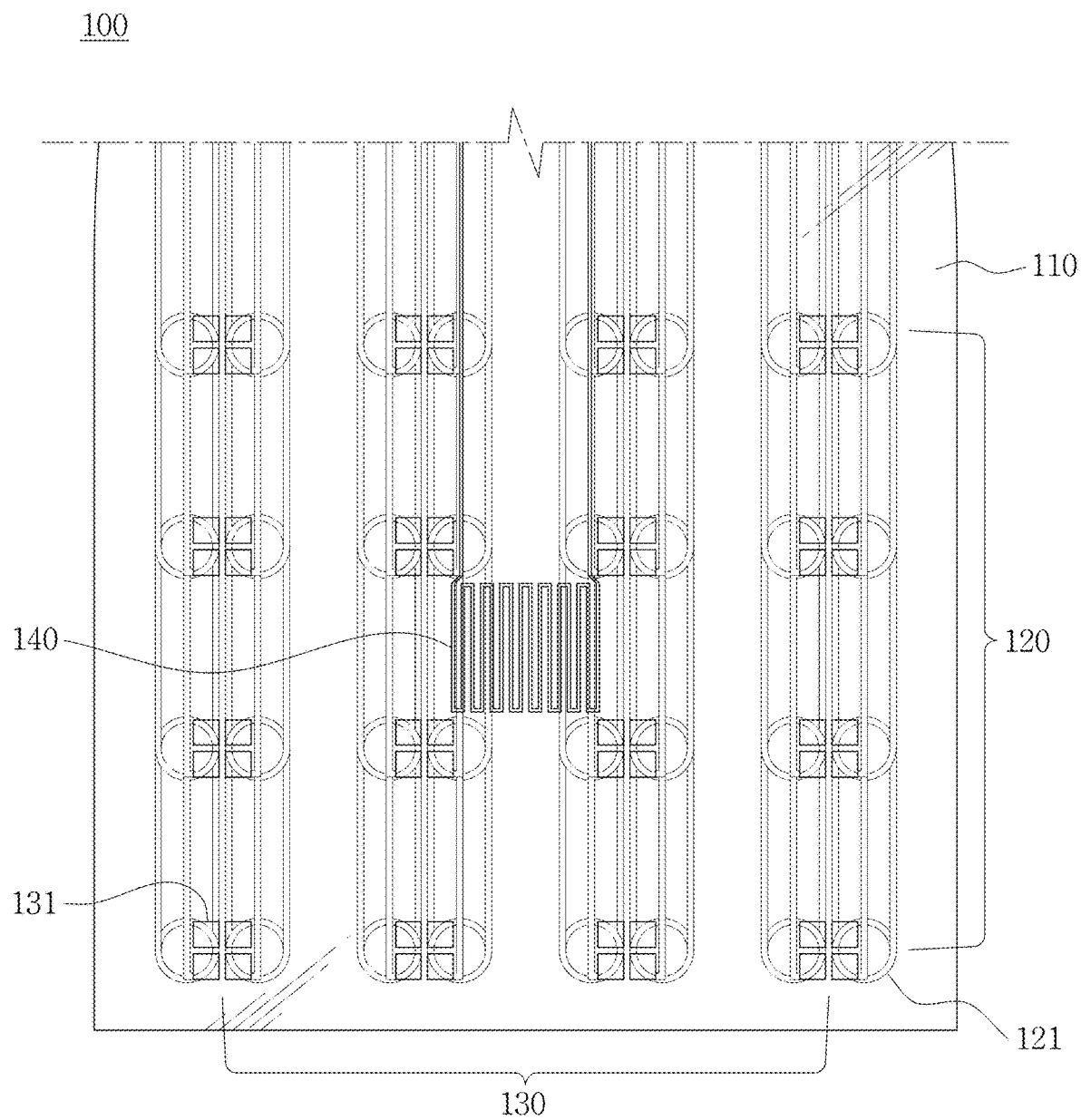
FIG. 1 is a plane view of a body stimulating structure according to an embodiment of the present disclosure.

Advantages and features of the present disclosure, and methods for achieving the same will be apparent from the embodiments described below with reference to the accompanying drawings. However, the present disclosure is not limited to the embodiments set forth therein and will be embodied in different forms, and these embodiments are provided so that the present disclosure will be thorough and complete and will fully convey the scope of the present disclosure to those skilled in the art, and the present disclosure is only defined by the appended claims.

The shape, size, ratio, angle, and number disclosed in the drawings to describe the embodiments of the present disclosure is for illustration only, and the present disclosure is not limited to the illustration. Furthermore, in describing the present disclosure, when details of relevant known technology are deemed to make the essence of the present disclosure ambiguous, its detailed description is omitted herein.

Unless 'only' is stated herein, 'including', 'having', and 'comprising' as used herein includes any additional component. Unless otherwise expressly provided herein, the singular forms include the plural forms.

The components are interpreted as having tolerances unless otherwise specified.

In the case of a description of a positional relationship, for example, 'on', 'above', 'below', and 'beside' that expresses a positional relationship between two parts, one or more other parts may be disposed between the two parts unless 'immediately' or 'directly' is used herein.

It will be understood that when an element or layer is referred to as being "on" another element or layer, it can be directly on the other element or layer or intervening elements or layers may be present. Like reference numerals denote like components throughout the drawings.

Although the terms first, second, etc. are used to narrate various components, it is obvious that these components are not confined by the terms. These terms are only used to distinguish one component from another. Accordingly, it is obvious that a first component stated hereinafter may be a second component within the technical spirit of the present disclosure.

The size and thickness of each component illustrated in the drawings is shown for convenience of description, and the present disclosure is not necessarily limited to the size and thickness of the components as shown.

Each feature of many embodiments of the present disclosure may be connected or combined with each other in part or in whole, and as fully understood by those skilled in the art, various interactions and operations can be technically accomplished, and each embodiment may work independently from each other and may work together in correlation.

Hereinafter, a body stimulating structure according to an embodiment of the present disclosure will be described with reference to the accompanying drawings.

Figure 2:
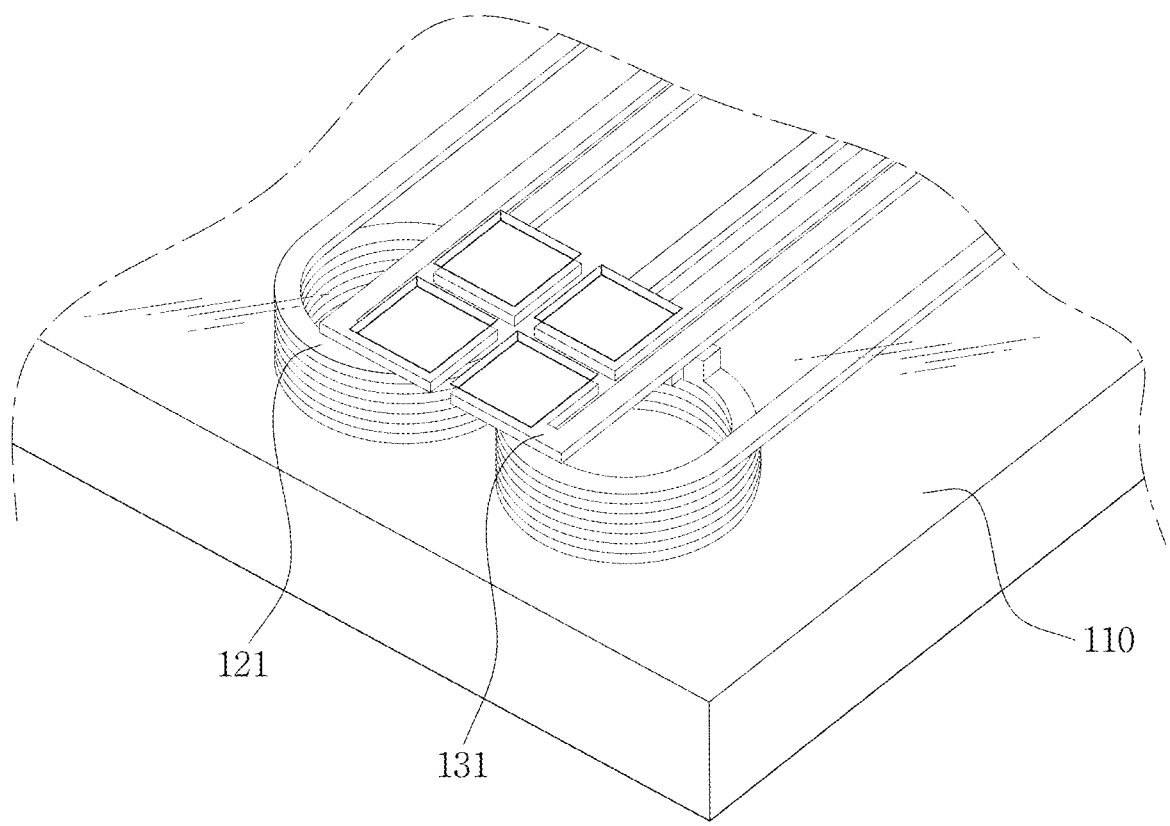
FIG. 2 is a partial enlarged view of the body stimulating structure of FIG. 1.
Figure 3:
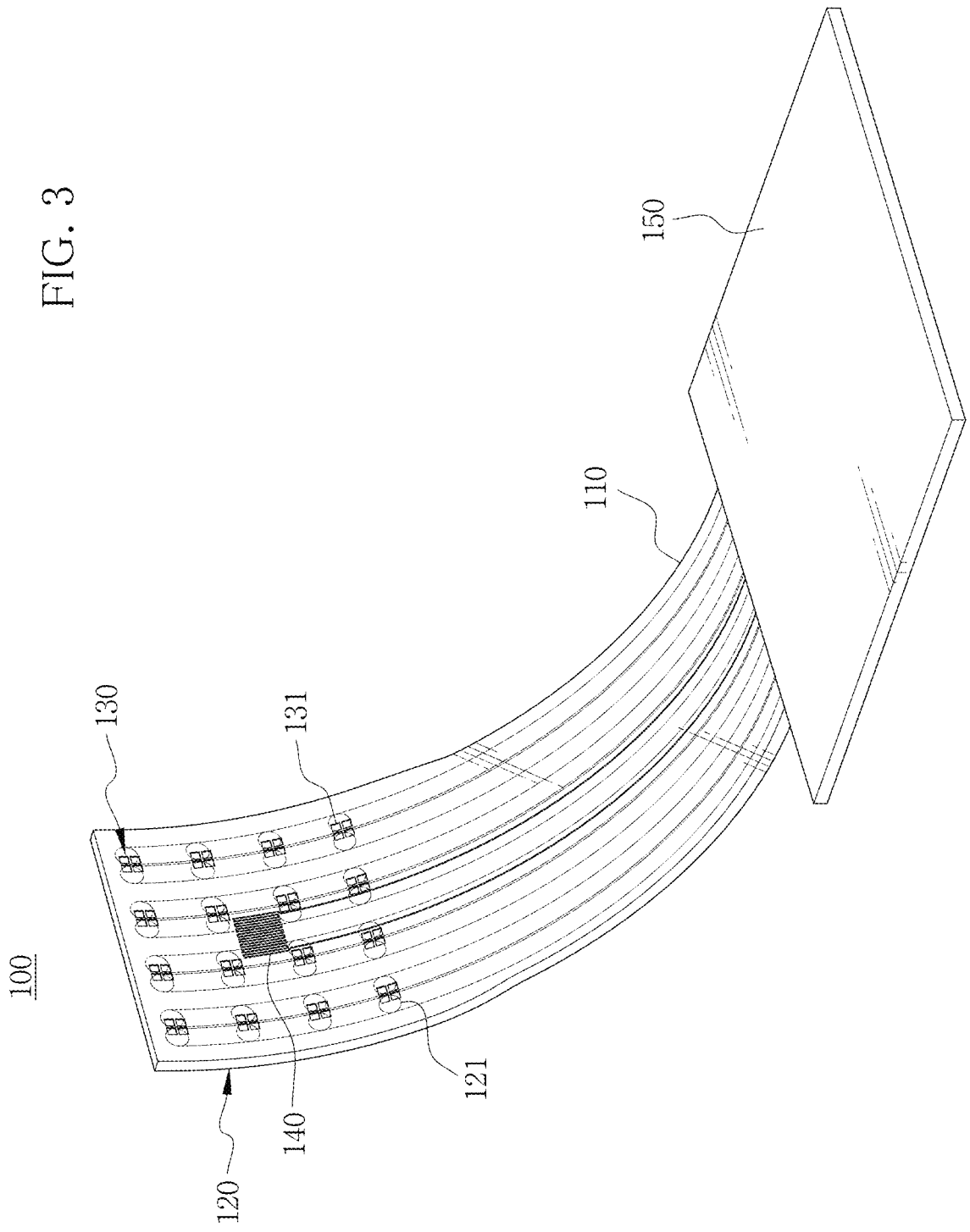
FIG. 3 is a perspective view of the body stimulating structure of FIG. 1.

Referring to FIGS. 1 to 3, the body stimulating structure 100 according to an embodiment of the present disclosure includes a body 110, a magnetic stimulation array 120, an electrode array 130, and a temperature sensor 140.

The body 110 is attached to an internal organ of a living body. The living body may be a human body or an animal body. The internal organ of the living body may include various organs. For example, the body 110 may be attached to the surface of the cerebral cortex within the skull. As such, the body 110 is attached to the internal organ of the living body to which magnetic stimulation needs to be applied or is to be applied.

The body 110 may be formed in the shape of a thin film. The body 110 may be attached to the internal part of the living body temporarily or semi-permanently, and thus, the body 110 is preferably so thin that it occupies minimum volume in order to reduce a foreign body sensation.

The body 110 may be made of a flexible material. For example, the body 110 may be made of a flexible polymer. Furthermore, the body 110 may be made of a flexible non-conductive material. On the other hand, because a magnetic field produced from the magnetic stimulation array 120 in the body 110 as described below needs to be transmitted to the internal organ of the living body outside the body 110, the body 110 is made of a material that does not shield a magnetic field.

Figure 4:
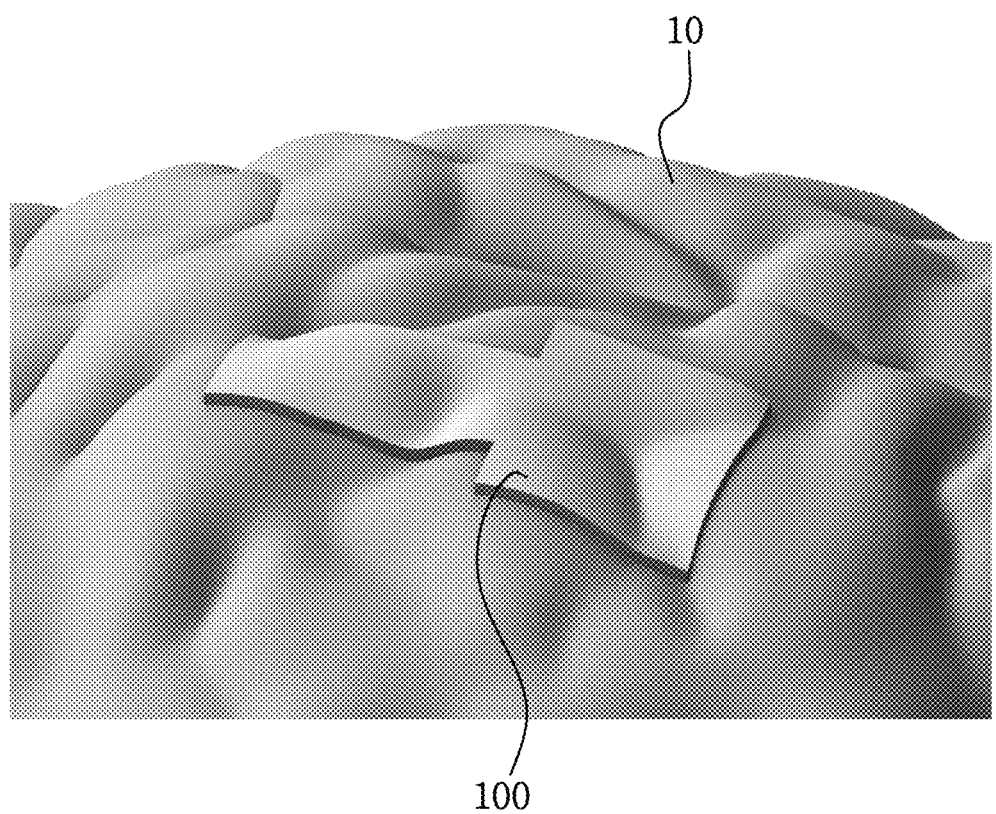
FIG. 4 is a schematic perspective view of the body stimulating structure of FIG. 1 attached to the surface of the cerebral cortex.

The body 110 can be effectively attached to the internal organ 10 of the living body such as the cerebral cortex having an uneven surface as shown in FIG. 4. Furthermore, the body 110 is attached to the internal organ of the living body over a relatively wide attachment area so that the body 110 can be stably fixed to the surface of the organ. Thereby, a magnetic field produced from the magnetic stimulation array 120 embedded in the body 110 as described below can be accurately applied to the internal organ 10 of the living body.

On the other hand, the body 110 may be formed in a very small size as compared to the internal organ of the living body. For example, the body 110 may be formed with the size of a few micrometers by a Micro-Electro-Mechanical System (MEMS) fabrication process. Accordingly, although FIG. 4 shows that the body 110 is attached to highly curved surfaces for convenience of understanding, the microscale body 110 may be attached to the surface of the internal organ of the living body that is slightly curved or is nearly close to the plane.

The magnetic stimulation array 120 is formed in the body 110. The magnetic stimulation array 120 is surrounded by the body 110 to prevent the direct contact with the internal organ of the living body. That is, as the magnetic stimulation array 120 is embedded in the body 110, the magnetic stimulation array 120 does not directly touch the internal organ of the living body.

The magnetic stimulation array 120 includes at least one coil 121. Each coil 121 produces a magnetic field when power is supplied. The coil 121 may be formed in various dimensions, taking in account the allowable intensity of the electric current and the number of turns of the coil 121. Thereby, an optimal intensity of magnetic field necessary for stimulation can be produced based on the type of the target internal organ of the living body. Rather, it should be noted that the magnetic stimulation array 120 may include various types of magnetic field inductors other than the coil 121 to apply magnetic stimulation to the target site to which the body 110 is attached.

The body stimulating structure 100 according to an embodiment of the present disclosure may include a plurality of coils 121. The plurality of coils 121 is arranged in parallel, spaced apart from each other. As shown, the plurality of coils 121 may be arranged to form square grid patterns spaced apart at a regular interval. The interval between each coil 121 may be appropriately selected based on the target organ to effectively transmit an independent stimulation. Furthermore, the interval between the coils 121 may be set in consideration of interference between magnetic fields generated by each coil 121. On the other hand, the plurality of coils 121 does not need to be arranged in the shown shape, and may be arranged in a variety of other patterns in consideration of the shape of the organ.

The plurality of coils 121 may be arranged such that the axial directions of the coils 121 are perpendicular to the surface of the internal organ of the living body to which the body 110 is attached. In this instance, the body 110 is preferably attached to the internal organ of the living body such that the axial directions of each coil 121 are perpendicular to the surface of the internal organ of the living body. That is, the axial directions of the plurality of coils 121 are each perpendicular to the attachment surface of the body 110, and the attachment surface of the body 110 is closely attached to the surface of the internal organ of the living body, so the plurality of coils 121 can be fixed such that the axial directions of each coil 121 are perpendicular to the surface of the internal organ of the living body. Thereby, a relatively large magnitude of magnetic field produced from an open end of the coil 121 along the axial direction of the coil 121 can be efficiently applied to the target site.

When the electric current flows in the coil 121 upon power supply, the magnetic field is formed around the coil 121. In the respect that the body stimulating structure 100 is attached to the internal part of the living body, it is advantageous that the coil 121 is wirelessly supplied with power from the outside through a wireless transmitting-receiving unit 150, but the body stimulating structure 100 may be connected to an external power supply (not shown) with a power transmitting-receiving line and be supplied with power.

The electric current may flow individually in each of the plurality of coils 121. That is, when the electric current flows in some of the plurality of coils 121, the electric current may not flow in the remaining coils 121. In this instance, the plurality of coils 121 may be individually supplied with power, and the electric current may be controlled by switching.

Thereby, when all or some of the plurality of coils 121 disposed adjacent to a desired site are selected and the electric current is allowed to flow, magnetic stimulation can be only applied to the desired site of the internal organ of the living body.

On the other hand, the direction of the magnetic field applied to the target site changes depending on the direction of the electric current flowing in the coil 121 and the direction in which the coil 121 is wound. Generally, the magnetic field around the coil 121 is formed, starting from one open end of the coil 121 turning around the outside of the coil 121 and then back to the other open end. The magnetic field by the coil 121 may be formed in various directions depending on the direction in which the coil 121 is placed in the body 110.

When the magnetic fields generated by each of the plurality of coils 121 are disposed close to each other, each magnetic field may interfere with each other and reinforce or cancel out each other. In view of this, two coils 121 may be placed side by side to form a pair at a location on the body 110. That is, each of the plurality of coils 121 may be placed close to each other as a pair at each location on the body 110. Thereby, each magnetic field by the pair of coils 121 reinforces each other at the target site, thereby increasing the focality of magnetic field at the target site.

For example, when the pair of coils 121 are placed such that each axial direction is parallel to each other and the electric current is allowed to flow such that the directions of each magnetic field face the opposite directions with respect to the axial direction, the magnetic fields may reinforce each other at the target site in front of the open end of the pair of coils 121, and the magnetic fields may cancel out each other at the remaining site. Thereby, the focality of magnetic stimulation at the target site can be increased. In this instance, the magnetic field of stronger strength is intensively formed between the coils 121, and the magnetic fields formed by each coil 121 in the remaining range are cancelled because of the opposite directions of the magnetic fields. Accordingly, when the body 110 is attached such that the target site is disposed between the two coils 121, magnetic stimulation can be intensively delivered to the target site, and the magnetic field applied to the remaining site can be minimized.

On the other hand, in case that the magnetic fields are pointing in the same direction for each coil 121 of which the axial directions are arranged in parallel to each other, the same effect as a large single coil 121 can be obtained.

On the other hand, in response to the magnetic stimulation by the magnetic stimulation array 120, a bio-signal generated from the internal organ of the living body is obtained by the electrode array 130. The electrode array 130 is provided in the body 110, and is placed such that part of the electrode 131 is exposed to the internal part of the living body.

The electrode array 130 includes at least one electrode 131. Each electrode 131 may be placed adjacent to each coil 121. As shown, the electrodes 131 may be placed corresponding to each position of the coils 121 arranged in parallel. Thereby, response signals may be individually obtained from each site stimulated by each coil 121. On the other hand, as only the desired site is selectively stimulated by each coil 121, response signals can be only obtained from the corresponding site. Through this, for example, the location of lesions can be individually determined with accuracy through selective magnetic stimulation. On the other hand, the response signals obtained through the electrode array 130 are transmitted to an external analysis means through the power transmitting-receiving line or the wireless transmitting-receiving unit 150 to analyze changes of the target site by the magnetic stimulation.

Electrical stimulation may be applied to the internal organ of the living body through the electrodes 131. Thereby, by use of one structure, the electrical stimulation can be applied to the internal organ of the living body through the electrode array 130, together with the magnetic stimulation by the magnetic stimulation array 120.

On the other hand, when the electric current flows in the magnetic stimulation array 120 and the electrode array 130, the coils 121 and the electrodes 131 generate heat. Thereby, the temperature of the target site to which the body 110 is attached may increase. The temperature sensor 140 provided in the body 110 can measure the temperature of the internal organ of the living body near the body 110.

The internal temperature of the living body is measured in real time through the temperature sensor 140, and when higher temperature than optimal is measured, the magnetic stimulation is stopped, thereby increasing stability of magnetic stimulation by the body stimulating structure 100.

On the other hand, the body stimulating structure 100 according to the present disclosure may further include means for other stimulation, for example, fluid stimulation and optical stimulation, to deliver various types of neural stimulation simultaneously.

Below is a description of a method for manufacturing the body stimulating structure 100 described above. A method of assuming the shape of the body stimulating structure 100 and forming electrodes on the body stimulating structure 100 may use known technique, and a method of embedding the coil 121 in the body stimulating structure 100 is mainly described in the specification.

The body stimulating structure 100 according to an embodiment of the present disclosure is manufactured by stacking a plurality of layers including the body 110 made from a wafer and the coil 121 made of a conducting metal material.

FIGS. 5A to 5G show the state of the body stimulating structure 100 at each step in the manufacture of the body stimulating structure 100 having the coil 121. On the other hand, it should be noted that only each part of one coil 121 in the magnetic stimulation array 120 is shown, and the body 110, the electrode array 130, and the temperature sensor 140 are omitted for convenience of description. Particularly, it should be understood that a dotted line represents a turn in the coil on a lower substrate hidden by a substrate stacked thereon.

Figure 5A:
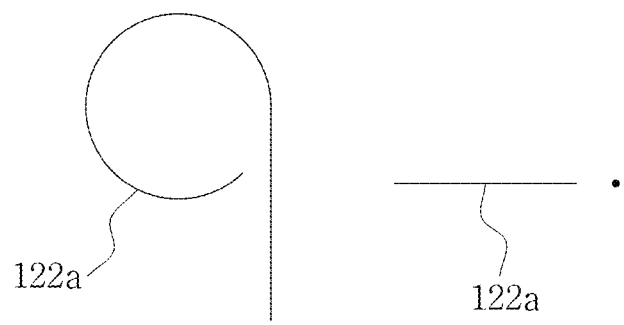
FIGS. 5A to 5G are schematic plane and side views showing the state at each step in the manufacture of the body stimulating structure of FIG. 1.

First, as shown in FIG. 5A, a first coil turn 122a of an open loop type forming the coil 121 and a power transmitting-receiving line connected thereto are deposited using a conductive material on a first pattern formed on a first substrate comprising the bottom of the body 110. In this instance, the first coil turn 122a has a cut-out part and is not completely continuous as shown.

Figure 5B:
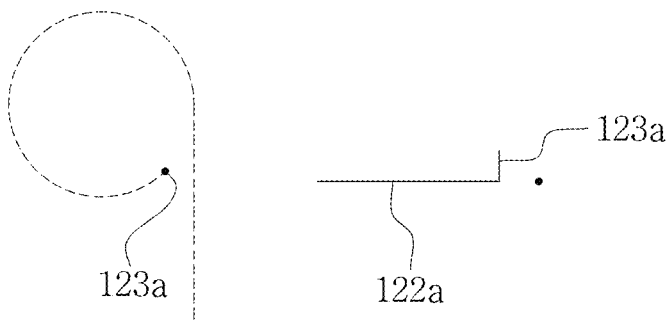

Subsequently, as shown in FIG. 5B, a second substrate including a first coil pillar 123a extending upwards from one end of the first coil turn 122a is further stacked on the first substrate. The first coil turn 122a and the first coil pillar 123a are electrically connected.

Figure 5C:
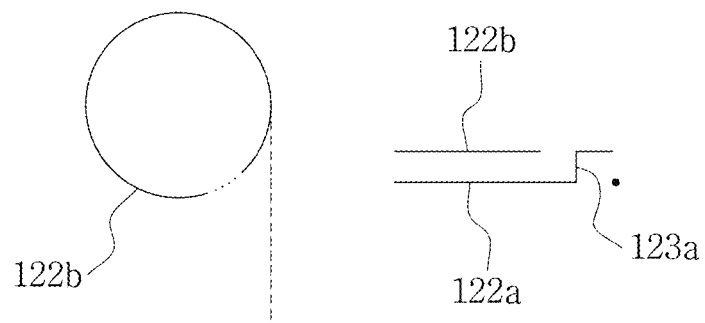

Subsequently, as shown in FIG. 5C, a third substrate is stacked on the second substrate, the third substrate including a second coil turn 122b placed adjacent to and parallel to the first coil turn 122a and the remainder portion completed with the material of the body 110. Thereby, the first coil turn 122a and the second coil turn 122b are electrically connected with the first coil pillar 123a. In this instance, the added second coil turn 122b extends from the top of the first coil pillar 123a and is not completely continuous with its cut-out part.

Figure 5D:
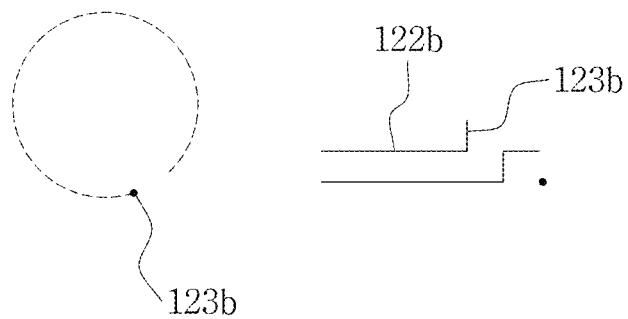

Subsequently, as shown in FIG. 5D, another substrate is further stacked, including a second coil pillar 123b electrically connecting the second coil turn 122b formed at the step of FIG. 5C to an adjacent third coil turn 122c that will be formed later and the remainder portion completed with the material of the body 110.

Figure 5E:
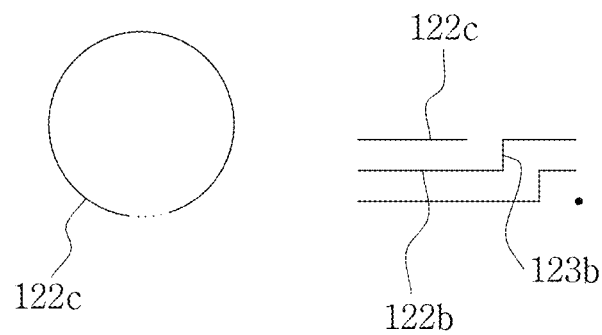
Figure 5F:
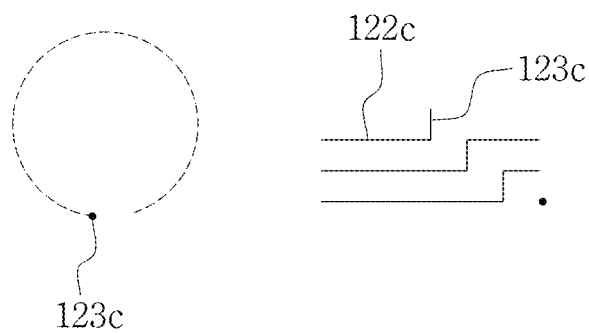

Subsequently, as shown in FIGS. 5E and 5F, the previous step is iteratively performed to stack substrates including the necessary number of coil turns and coil pillars such as a third coil pillar 123c. That is, one or more substrates including one of the remaining coil turns of the coil 121 of an open loop type and coil pillars electrically connecting each coil turn in an alternating manner are stacked in a sequential order, to manufacture the body 110 comprising the coil 121 of multiple turns embedded therein.

Figure 5G:
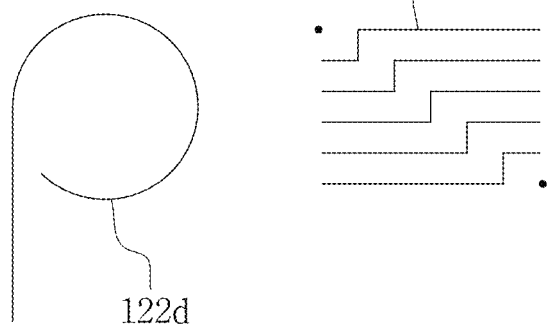

Finally, as shown in FIG. 5G, a top substrate is stacked, in which a topmost coil turn 122d and a power transmitting-receiving line connected thereto are deposited. Subsequently, although not shown, the coil 121 and the wireless transmitting-receiving unit 150 or the power transmitting-receiving electrode are connected to complete a circuit connected to the coil 121.

Additionally, the body 110, on which the circuit is formed, including the electrode array 130 and the temperature sensor 140, is patterned and released to complete the body stimulating structure 100 including the coil 121 according to an embodiment of the present disclosure.

On the other hand, although FIGS. 5A to 5G show that each coil turn 122a, 122b, 122c, 122d has a circular shape, each coil turn 122a, 122b, 122c, 122d may have any polygonal shape, for example, a square shape. Furthermore, discontinuous gaps of each coil turn 122a, 122b, 122c, 122d may be formed at various intervals and positions. Accordingly, the positions of the coil pillars 123a, 123b, 123c may also differ. Furthermore, the length of each coil pillar 123a, 123b, 123c may be also set appropriately in consideration of the thickness of the body 110 and the necessary number of coil turns.

As shown, the coil 121 is manufactured by a stacking method using a photo resist, thereby manufacturing the body stimulating structure 100 with high yield. Particularly, in the case of a general coil, the height continuously increases with the increasing number of turns, for example, in a spiral shape, but the coil 121 in this example can be easily manufactured by a stacking method having a uniform thickness with a discontinuously increasing height due to the steps.

Although the embodiments of the present disclosure have been hereinabove described in further detail with reference to the accompanying drawings, the present disclosure is not necessarily limited to these embodiments, and modifications may be made thereto in various forms without departing from the technical spirit of the present disclosure. Accordingly, the embodiments disclosed in the present disclosure are provided to describe the technical spirit of the present disclosure, but are not intended to limit the technical spirit of the present disclosure, and the scope of the technical spirit of the present disclosure is not limited by these embodiments. Therefore, it should be understood that the embodiments described hereinabove are illustrative, but are not limitative, in all aspects. The scope of protection of the present disclosure should be interpreted by the appended claims, and the full technical spirit within the scope in equivalence thereto shall be interpreted as being included in the scope of protection of the present disclosure.

What is claimed is:

1. A body stimulating structure comprising:
   a body configured to be attached to an internal organ of a living body; and
   a magnetic field inductor formed in the body,
   wherein when power is supplied, the magnetic field inductor produces a magnetic field and applies magnetic stimulation to a target site of the internal organ of the living body if the body is attached to the living body,
   the magnetic field inductor includes a plurality of coils arranged in parallel, spaced apart from each other, and
   each of the plurality of coils is placed closer to another coil of the plurality of coils than the other coils of the plurality of coils to be operated as a pair with the another coil,
   wherein each of the plurality of coils includes a first coil turn of an open loop type with a uniform height and a first coil pillar extending upwards from one end of the first coil turn.

2. The body stimulating structure according to claim 1, wherein the plurality of coils is arranged such that axial directions of the coils are perpendicular to a surface of the internal organ of the living body to which the body is attached.

3. The body stimulating structure according to claim 1, wherein an electric current flows individually in the plurality of coils, and
   all or some of the plurality of coils are selected to apply magnetic stimulation to the internal organ of the living body.

4. The body stimulating structure according to claim 1, wherein the body is made of a flexible material.

5. The body stimulating structure according to claim 4, wherein the body is configured to be attached to the internal organ of the living body such that axial directions of the coils are perpendicular to a surface of the internal organ of the living body.

6. The body stimulating structure according to claim 1, further comprising:
   an electrode provided in the body to obtain a bio-signal generated in response to the magnetic stimulation.

7. The body stimulating structure according to claim 6, wherein electrical stimulation is applied to the internal organ of the living body through the electrode.

8. The body stimulating structure according to claim 1, further comprising:
   a temperature sensor provided in the body to measure an internal temperature of the living body.

9. The body stimulating structure according to claim 1, wherein each of the plurality of coils further includes a second coil turn of the open loop type with a uniform height, extending from a top of the first coil pillar, having a same area with the first coil turn, and stacked on the first coil turn.

10. The body stimulating structure according to claim 9, wherein each of the plurality of coils further includes a second coil pillar extending upwards from one end of the second coil turn, and the second coil pillar does not overlap the first coil pillar in a top view.

11. A method for manufacturing a body stimulating structure, in which the body stimulating structure is defined in claim 1, the method comprising:
    forming a first pattern on a first substrate, and filling the first pattern with a conductor;
    stacking a second substrate on the first substrate; and
    forming a second pattern connected to the first pattern on the second substrate, and filling the second pattern with a conductor,
    wherein the first substrate and the second substrate form the body, and
    the conductor of the first pattern and the conductor of the second pattern form a part of the magnetic field inductor.

12. The method for manufacturing a body stimulating structure according to claim 11, wherein the magnetic field inductor is formed in a shape of the coil.

13. The method for manufacturing a body stimulating structure according to claim 12, wherein the conductor of the first pattern is the first coil turn,
    the conductor of the second pattern is the first coil pillar, and
    the method further comprises stacking one or more substrates including one of remaining coil turns of the coil of an open loop type and coil pillars electrically connecting each coil turn in an alternating manner on the second substrate in a sequential order.

* * * * *